United States Patent [19]

Lazarev et al.

[11] Patent Number: 5,397,578
[45] Date of Patent: Mar. 14, 1995

[54] METHOD OF TREATMENT OF CHRONIC PURULENT INFLAMMATIONS OF EAR IN CHILDREN

[75] Inventors: Vyacheslav N. Lazarev; Alexandr S Skryabin; Alexei J. Ivoilov, all of Moscow

[73] Assignee: Tovarischestvo s ogranichennoi otvetstvennostiju "Taurus", Moscow, Russian Federation

[21] Appl. No.: 219,673

[22] Filed: Mar. 29, 1994

[51] Int. Cl.⁶ .................. A61K 33/14; A61K 35/16
[52] U.S. Cl. .................. 424/680; 424/164.1; 424/520; 424/529; 424/530; 424/531
[58] Field of Search ............. 424/85.8, 520, 529, 424/530, 531

[56] References Cited

PUBLICATIONS

Fedorova et al SU 1560199 (Apr. 30, 1990).
Alekseera et al SU 1197672 (Dec. 15, 1985).
Bikbaeva et al SU 1242179 (Jul. 7,1986).
Shurin et al J. Pediatr. 123(5). 739–741 Nov. 1993.
Stever et al Oto–Rhino–Laryneol Nova 4/2: 76–81(1994).
Griguryer et al USSR Vestn. Ottoringlaringol 43/2: 13–15(1981).
Brief Medical Encyclopaedia, Moscow, vol. 2, p. 314 in Russian & English (1989).
Hypoacusis, p. 383 in Russian & English (1978).

*Primary Examiner*—Shep K. Rose
*Attorney, Agent, or Firm*—Ladas & Parry

[57] ABSTRACT

A method for treating chronic, purulent, middle otitis in children, comprising administering, through a perforation into a middle ear cavity, a freshly prepared donor plasma of one of the parents having the identical blood group to fill up the cavity (1,5–2,0 ml 3–4 times within 24 hours with the preliminary washing of the cavity with a physiological solution prior to each administration.

2 Claims, No Drawings

METHOD OF TREATMENT OF CHRONIC PURULENT INFLAMMATIONS OF EAR IN CHILDREN

FIELD OF THE INVENTION

The invention relates to medicine, more specifically, to otorinolaringology, treatment of chronic purulen inflammations of ear in children.

BACKGROUND OF THE INVENTION

Known in the art are methods for treatment of purulent middle otitis (inflammation of ear) by locally using various liquid drugs, such as antibiotics which not infrequently cause allergic reactions (especially with children), sharply suppress immunity and also promote the development of antibiotic resistive power of microflora (Concised medical encyclopaedia, edit. by B. Petrovsky, Moscow, 1989, vol. 2 p.314).

Moreover, some antibiotics to which microflorae are sensitive (neomycin, streptomycin, gentamycin) display an ototoxic effect i.e. not only impair hearing functions, but also can result in the complete hearing loss.

In the book "Hardness of hearing", Moscow, Meditsina, 78, p.383, I. Soldatov describes the treatment of purulent otites by using proteolytic enzymes, such as trypsin and chymotrypsin. Substantial defects of these methods are duration of treatment, frequent allergic reactions and limitedness of action.

Currently known is the role leucocytes and plasma components have to play in various inflammation diseases. In USSR inventor's certificate N 119 7672, V. Kirillov et al. there is described a method of treatment of bronchial pulmonary diseases with donor leucomass, in which case there are observed frequent allergic reactions. For this very reason, it is proposed that autoleucomass should be employed.

The prototype of the present invention is the local application of an autoleucocytic mass for the treatment of the purulent inflammable diseases of the middle ear in grown-up patients, which is described in inventorship certificate No.1560199, Skryabin et al. This method is useless for children because the preparation of said autoleucomass calls for the daily collection of blood (10-15 ml) from the ulnar vein, which is impossible in the case of children.

SUMMARY OF THE INVENTION

For elimination of all the above-listed disadvantages, use is made of a new method of treatment for children suffering from chronic purulent, difficultly yielding to treatment, middle otites.

An object of the invention is the new method of treatment of children having purulent otitis, comprising the steps of a local application of donor plasma thanks to its highly efficient antiphlogistic and antibacterial effect.

In order to completely preclude allergic reactions in children, use is made of a plasma obtained from the blood of a parent having a blood group identical with the patient's.

An object of the invention is to improve the efficiency of treatment of said purulent otitis with simplification of the method of treatment.

Said object is attained owing to the fact that the method provides for administering, though a perforation into a middle ear cavity, a liquid medicine.

Said medicine is represented by a freshly prepared donor plasma from the parent with the identical blood group to fill up the cavity (1,5-2,0 ml) four times a day by preliminarily washing the cavity with a physiological solution before each administration.

DETAILED DESCRIPTION OF THE INVENTION

The method is carried out in the following manner.

Some 15 ml of blood, supported on heparin (20 unit/ml) are taken daily from a donor-parent having a blood group identical with that of the sick child, from the properly sterilized ulnar vein, which is then centrifuged at 3000 rev/min for 15 minutes, whereupon a supernatant liquid is taken that is precisely a donor plasma. Treatment is begun not later than one hour after the plasma has been obtained. Into the middle ear cavity, washed with a physiological solution, through a perforation (with the aid of an attic cannula or under pressure) the parent's plasma is administered into the tympanum to be left there up to a next administration. Prior to each administration, the middle ear cavity is washed with the physiological solution, the procedure being repeated 3-4 times a day (24 hrs) and a course of treatment lasting from 4 to 7 days.

The utilization of plasma during 24 hours is necessitated by the fact that practically all antiphlogistic factors are preserved therein during this period of time in an active state, quite a number of which loosing their activity, upon storage over 24 hours (complement and so on).

Control over treatment is exercized through use of three parameters:

1) Visual observance of the termination of suppuration from the ear (down to relieving the process).
2) A patient is under survey for six months to one year for the purpose of performing an operation—myringoplasty or improvement of hearing (in the case of conductive or mixed forms of hardness of hearing).
3) Audiologic control (in the presence of a neurosensory component on an audiogram use is made of stimulating and vitamin therapy, a course using the fluctuating currents).

An advantage of the present method resides in a sharp improvement of efficiency of treatment of purulent middle otitis in children due to a great number of antiphlogistic and antibacterial factors comprising the fresh plasma.

The method was used on 67 children with purulent middle otitis (12 children—epitympanitis, 17—epimesotympanitis and 38—mesotympanitis) aged 3 years and 7 months to 14 years and II months. An analysis (distant results) performed during I-I,5 years has revealed aggravation of a chronic purulent process in the tympanum of five children (4—epitympanitis, I—epimesotympanitis).

The authors believe that the main cause of aggravation was the presence of the attic-anthral cavity of a cholesteatoma block (visually cholesteatoma scales were not detected in washing) and also a relatively low level of secreting forms JgA (SJgA) (traces-0,001 g/l) and a neutrophile link of cells ($\epsilon$-Pok up to 5% and D-phagocytosis—up to II%) in the focus of inflammation.

The method was used on 41 patients.

The method is illustrated by the examples as cited hereinbelow.

EXAMPLE I.

Case history N 1003. Patient K, 12, was admitted to the department of childrens' clinic No.9, Moscow, with the diagnosis of double chronic, purulent otitis. Suffering from the disease for II years. Stayed in the hospital 2-3 times a year. In 1985 a radical operation was performed on the left ear with a very short-lived improvement (a month and a half). Later the child was admitted to the hospital with purulent discharge from both ears. Treatment with a donor plasma from his mother, blood group B (III), neg. Rh. Said mother's plasma was admistered, 3 times a day, into the right ear through a perforation in the tympanum with the aid of an attic cannula, and into the left ear by washing the post-operation cavity. On the fourth day, suppuration stopped, and seven days after the beginning of a treatment course, the child was discharged from the hospital practically sound. Control examination was performed five months after—no pathological changes in the middle ear cavity.

EXAMPLE 2.

Case history N 3437. Patient M., 9, admitted to the hospital with the diagnosis of left-side chronic purulent middle otitis.

Suffering from the disease since the age of an year and a half Underwent treatment in various hospitals, conservative courses. After ineffective treatment with reserve antibiotics, hydrocortisone, dioxidine, the patient was treated with a donor plasma (the father's). Suppuration stopped completely on the third day and the middle ear cavity was dry on the fifth day. The child was discharged seven days after the beginning of treatment with the donor plasma in a satisfactory state. Effective treatment, because after six months, the control inspection revealed that no pathological changes had been present in the middle ear cavity.

The method per se has brought about a positive effect in practically all the patients. On the third-fourth days of treatment with the donor plasma, acute improvement set in with the patients as compared to those undergoing an ordinary course of treatment. The method in question can be used in all otorinolaringologic departments of hospitals and clinics. An economic effect consists in reducing the time of treatment, comparable to other methods, 2-5 times over, as well as in complete absence of expenditures on medicinal preparations.

What is claimed is:

1. A method for treating chronic purulent, middle otitis, comprising the preliminary washing of the cavity of the middle ear in a physiological solution and the subsequent administration of the blood plasma of a parent with the identical blood group into the tympanum through a perforation by using an attic cannula or under pressure.

2. A method in accordance with claim 1, characterized in that said plasma is administered into said tympanum in an amount of between 1,5 and 2,0 ml 3-4 times within 24 hours.

* * * * *